(12) United States Patent
Horiike

(10) Patent No.: US 8,425,842 B2
(45) Date of Patent: Apr. 23, 2013

(54) SUPPRESSOR AND ION CHROMATOGRAPH EMPLOYING THE SAME

(75) Inventor: Shigeyoshi Horiike, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 479 days.

(21) Appl. No.: 12/811,322

(22) PCT Filed: Jan. 7, 2008

(86) PCT No.: PCT/JP2008/050009
§ 371 (c)(1),
(2), (4) Date: Jun. 30, 2010

(87) PCT Pub. No.: WO2009/087751
PCT Pub. Date: Jul. 16, 2009

(65) Prior Publication Data
US 2010/0284861 A1 Nov. 11, 2010

(51) Int. Cl.
*G01N 30/02* (2006.01)
*G01N 30/84* (2006.01)
(52) U.S. Cl.
USPC .......... 422/70; 422/534; 210/198.2; 73/61.52
(58) Field of Classification Search .................... 422/70; 210/198.2, 656; 436/160; 73/61.52–61.58
See application file for complete search history.

(56) References Cited

U.S. PATENT DOCUMENTS

| | | |
|---|---|---|
| 4,999,098 A | 3/1991 | Pohl et al. |
| 5,352,360 A | 10/1994 | Stillian et al. |
| 6,077,434 A | 6/2000 | Srinivasan et al. |
| 6,814,859 B2 * | 11/2004 | Koehler et al. ............ 210/198.2 |
| 2002/0192832 A1 | 12/2002 | Anderson et al. |

FOREIGN PATENT DOCUMENTS

CN 1403811 A 3/2003
(Continued)

OTHER PUBLICATIONS

The First Office Action for the Application No. 200880122785.2 from The State Intellectual Property Office of the People's Republic of China dated Jul. 17, 2012.

(Continued)

*Primary Examiner* — Jan Ludlow
(74) *Attorney, Agent, or Firm* — Cheng Law Group, PLLC

(57) ABSTRACT

A suppressor which comprises: an ion-exchange membrane; an eluate channel which is in contact with one side of the ion-exchange membrane, serves as a channel through which an eluate discharged from a separation column flows, and has inside no obstacle to the flow; a regenerant channel which is in contact with the other side of the ion-exchange membrane, serves as a channel through which a regenerant for regenerating ionic functional groups of the ion-exchange membrane flows, has been disposed so that the regenerant channel has no region facing the eluate channel and extends in parallel to the eluate channel in such a nearby position that the ionic functional groups can move through the ion-exchange membrane, and has inside no obstacle to the flow; and an ion-exchange membrane support member which is in contact at least with that region on one side of the ion-exchange membrane which is opposed to the regenerant channel and with that region on the other side of the ion-exchange membrane which is opposed to the eluate channel to thereby support the ion-exchange membrane with wall surfaces.

10 Claims, 5 Drawing Sheets

FOREIGN PATENT DOCUMENTS

| | | |
|---|---|---|
| CN | 101044399 A | 9/2007 |
| JP | 61-172057 A | 8/1986 |
| JP | 1-169353 A | 7/1989 |
| JP | 3-87657 A | 4/1991 |
| JP | 2001-194353 A | 7/2001 |
| JP | 2002-214212 A | 7/2002 |
| JP | 2002-535618 A | 10/2002 |

OTHER PUBLICATIONS

International Search Report for the Application No. PCT/JP2008/050009 mailed Feb. 5, 2008.

Sekiguchi, Yoko et al., "Shinhoshiki Ion Kanryugata Suppressor no Rinri to Oyo", 17th Chromatography Forum: Lecture Summary, 2000, pp. 30-31.

* cited by examiner

SUPPRESSOR AND ION CHROMATOGRAPH EMPLOYING THE SAME

BACKGROUND OF THE INVENTION

1. Field of the Invention

The present invention relates to an ion chromatograph for separation and analysis of inorganic ions or organic ions contained in a sample solution and a suppressor for suppressing the background electrical conductivity of an eluate discharged from a separation column of such an ion chromatograph.

2. Description of the Related Art

In an ion chromatograph, a sample is introduced into a separation column to separate it into component ions, and then the component ions are detected by measuring the electrical conductivity of an eluate discharged from the separation column in an electrical conductivity measurement cell. In order to achieve high-sensitive measurement, a suppressor is provided between the separation column and the detector. The suppressor removes nontarget ions contained in an eluate discharged from the separation column to reduce the electrical conductivity of the eluate.

As such a suppressor, one using an ion-exchange membrane is conventionally used. An example of a conventional suppressor is shown in FIGS. 7A and 7B. FIG. 7B is a sectional view of the conventional suppressor shown in FIG. 7A taken along the X-X line. A channel 104 through which an eluate discharged from a separation column flows, and a channel 106 through which a regenerant for regenerating ionic functional groups of an ion-exchange membrane 102 flows are arranged so as to be opposed to each other through the ion-exchange membrane 102. Base bodies 108 and 110 are arranged so that the channels 104 and 106 are opposed to each other with the ion-exchange membrane 102 being interposed between them.

The channels 104 and 106 are merely hollow channels through which liquid flows. The ion-exchange membrane 102 has low stiffness, and therefore, when the pressure in the channel 104 and the pressure in the channel 106 are changed due to a change in the back pressure of the suppressor, and thus, a large difference is caused between the pressure in the channel 104 and the pressure in the channel 106, the ion-exchange membrane 102 is displaced toward one of the channels due to pressure exerted on the ion-exchange membrane 102. The displacement of the ion-exchange membrane 102 causes changes in the volumes of the channels 104 and 106, and as a result, the amount of nontarget ions removed from an eluate fluctuates and therefore the base line of a chromatogram becomes unstable.

In order to prevent such displacement of the ion-exchange membrane, a suppressor obtained by filling the channels 104 and 106 with an ion-exchange resin as a filler (see JP-A-1-169353) and a suppressor obtained by filling the channels 104 and 106 with a cross-linked material (see JP-A-61-172057) have been proposed.

In a method for filling channels with a filler, such as the proposed suppressor, pressure losses in the channels are increased by the filler and therefore, liquid feed pressures need to be increased. This, however, increases the load on the ion-exchange membrane, which may cause disadvantages, such as leakage of liquid from parts fixing the ion-exchange membrane.

Further, in a case where the filler is an ion-exchange resin, there is a case where a difference in performance is caused among individual suppressors due to variations in the characteristics of the ion-exchange resin or the activity of the ion-exchange resin is changed due to repeated use so that changes in ion chromatogram occur with time.

SUMMARY OF THE INVENTION

It is therefore an object of the present invention to provide a suppressor capable of preventing the displacement of an ion-exchange membrane without filling its channels with a filler and an ion chromatograph employing such a suppressor.

As the present invention, a suppressor for suppressing the background electrical conductivity of an eluate discharged from a separation column of an ion analyzer, including an ion-exchange membrane; an eluate channel, which is in contact with one side of the ion-exchange membrane, serves as a channel through which an eluate discharged from the separation column flows and has inside no obstacle to the flow; a regenerant channel, which is in contact with the other side of the ion-exchange membrane, serves as a channel through which a regenerant for regenerating ionic functional groups of the ion-exchange membrane flows, has been disposed so as to have no region facing the eluate channel and to extend in parallel to the eluate channel in such a nearby position that the ionic functional groups can move to the eluate channel through the ion-exchange membrane and has inside no obstacle to the flow; and an ion-exchange membrane support member, which is in contact with at least a region on one side of the ion-exchange membrane which is opposed to the regenerant channel and a region on the other side of the ion-exchange membrane, which is opposed to the eluate channel, to support the ion-exchange membrane with wall surfaces.

The region opposed to the eluate channel, which is on the other side of the ion-exchange membrane opposite to the one side of the ion-exchange membrane, which is in contact with the eluate channel, is supported by the wall surface of the ion-exchange membrane support member, and a region opposed to the regenerant channel, which is on the one side of the ion-exchange membrane opposite to the other side of the ion-exchange membrane which is in contact with the regenerant channel, is also supported by the wall surface of the ion-exchange membrane support member. This makes it possible to prevent the displacement of the ion-exchange membrane toward the eluate channel and the regenerant channel even when the pressure in the eluate channel and the pressure in the regenerant channel are changed, or a pressure difference between these channels is changed.

The eluate channel and the regenerant channel are arranged in such a nearby position that ionic functional groups can move through the ion-exchange membrane. This makes it possible for the suppressor to maintain its ion exchange function, that is, the function of exchanging nontarget ions with the ionic functional groups, and act as a suppressor. In a case where the ion-exchange membrane is a cation exchange membrane, the ionic functional groups are hydrogen ions ($H^+$). In a case where the ion-exchange membrane is an anion exchange membrane, the ionic functional groups are hydroxide ions ($OH^-$).

According to a preferable embodiment, the suppressor has a laminate structure in which the ion-exchange membrane is interposed between two base bodies. In this case, the eluate channel is provided in one of the two base bodies so as to have an inlet and an outlet and to be in contact with the ion-exchange membrane, the regenerant channel is provided in another base body so as to have an inlet and an outlet and to be in contact with the ion-exchange membrane, and the ion-exchange membrane support member is composed of part of the two base bodies, which are in contact with the ion-exchange membrane.

The regenerant channel may be provided on the same surface of the ion-exchange membrane so as to be located on opposite sides of the eluate channel.

According to another embodiment, the ion-exchange membrane is composed of two first and second ion-exchange membranes, the eluate channel is interposed between the two ion-exchange membranes so that two sides of the eluate channel are in contact with these ion-exchange membranes, and the regenerant channel is provided for each of the ion-exchange membranes. In this case, the regenerant channel may be provided on the same surface of at least one of the ion-exchange membranes so as to be located on opposite sides of the eluate channel.

According to a preferable embodiment, the suppressor having two ion-exchange membranes has a laminate structure in which the first ion-exchange membrane is in contact with one side of a first base body and is interposed between the first base body and a second base body, and the second ion-exchange membrane is in contact with the other side of the first base body and is interposed between the first base body and a third base body. In this case, the eluate channel is provided in the first base body as a groove penetrating in the thickness direction of the first base body, the regenerant channel is composed of a first regenerant channel provided in the second base body so as to have an inlet and an outlet and to be in contact with the first ion-exchange membrane, and a second regenerant channel provided in the third base body so as to have an inlet and an outlet and to be in contact with the second ion-exchange membrane, and the ion-exchange membrane support member is composed of part of the first, second, and third base bodies, which are in contact with the first or second ion-exchange membrane.

The suppressor may be used singly, but a multistage suppressor may be produced by connecting two or more suppressors to each other. In this case, the multistage suppressor is provided in a channel through which an eluate discharged from a separation column flows, and the outlet of the eluate channel of the upstream suppressor is connected to the inlet of the eluate channel of the downstream suppressor.

An ion chromatograph employing the suppressor according to the present invention includes: a separation column; an eluent supply channel for supplying an eluent to the separation column; an injector provided in the eluent supply channel to inject a sample into the eluent supply channel; an electrical conductivity detector provided in an eluate channel through which an eluate discharged from the separation column flows; and the suppressor according to the present invention provided in the eluate channel from the separation column between the separation column and the electrical conductivity detector.

In a suppressor according to the present invention and an ion chromatograph employing such a suppressor, one side of an ion-exchange membrane opposite to the other side of the ion-exchange membrane, which is in contact with an eluate channel, is supported by an ion-exchange membrane support member, and the other side of the ion-exchange membrane opposite to the one side of the ion-exchange membrane, which is in contact with a regenerant channel, is also supported by the ion-exchange membrane support member, and therefore, the displacement of the ion-exchange membrane toward one of the eluate channel and the regenerant channel can be prevented without filling these channels with a filler. Further, since the eluate channel and the regenerant channel are not filled with a filler, it is not necessary to increase liquid feed pressures, thereby preventing liquid leakage caused by excessive pressure exerted on the ion-exchange membrane.

DETAILED DESCRIPTION OF THE INVENTION

Figure 1:
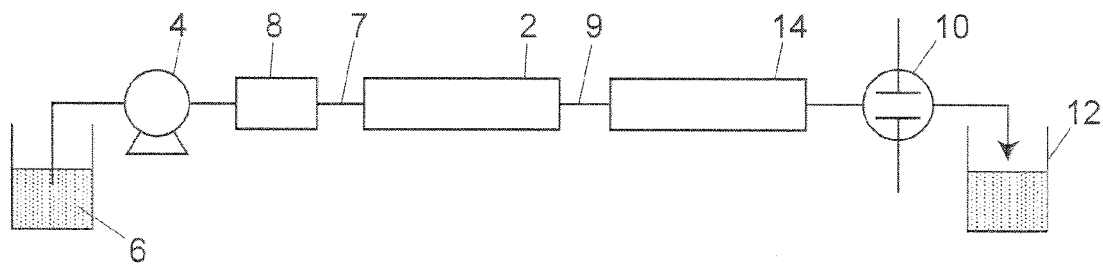
FIG. 1 is a diagram showing the channels of an ion chromatograph according to one embodiment of the present invention.

FIG. 1 is a schematic diagram of one embodiment of an ion chromatograph according to the present invention. A liquid channel 7 equipped with a liquid pump 4 for supplying an eluent 6 is connected to a separation column 2. The liquid channel 7 is equipped also with an injector 8 for injecting a sample. A sample is introduced into the separation column 2 and separated into individual ions. The eluate channel 9 is guided from the separation column 2 to an electrical conductivity measurement cell 10. The electrical conductivity of the eluate is detected when the eluate passes through the cell 10. Effluent from the cell 10 is discharged into a drain 12.

The eluate channel 9 connecting the separation column 2 to the cell 10 is equipped with a suppressor 14 to remove non-target ions causing an increase in the electrical conductivity of a column eluate to achieve high-sensitive measurement.

Figure 2A:
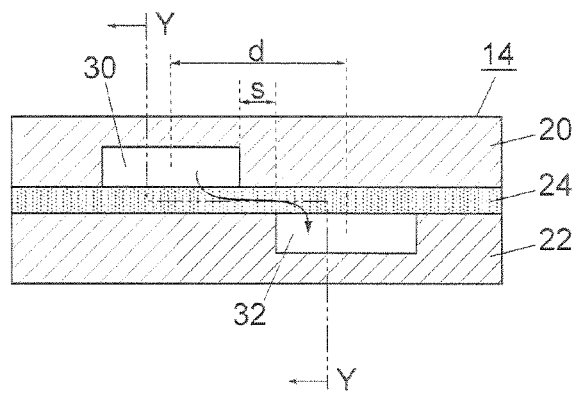
FIG. 2A is a sectional view of a suppressor according to one embodiment of the present invention, taken along a direction perpendicular to the longitudinal direction of channels.
Figure 2B:
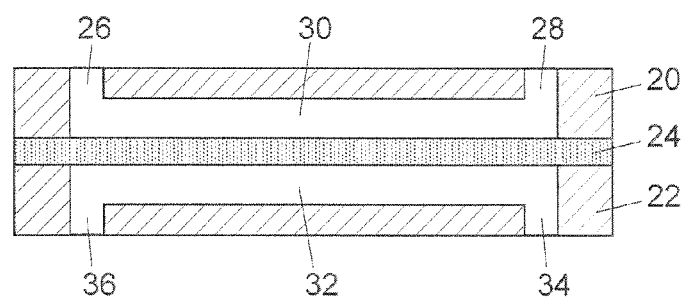
FIG. 2B is a sectional view of the suppressor shown in FIG. 2A, taken along the Y-Y line.
Figure 2C:
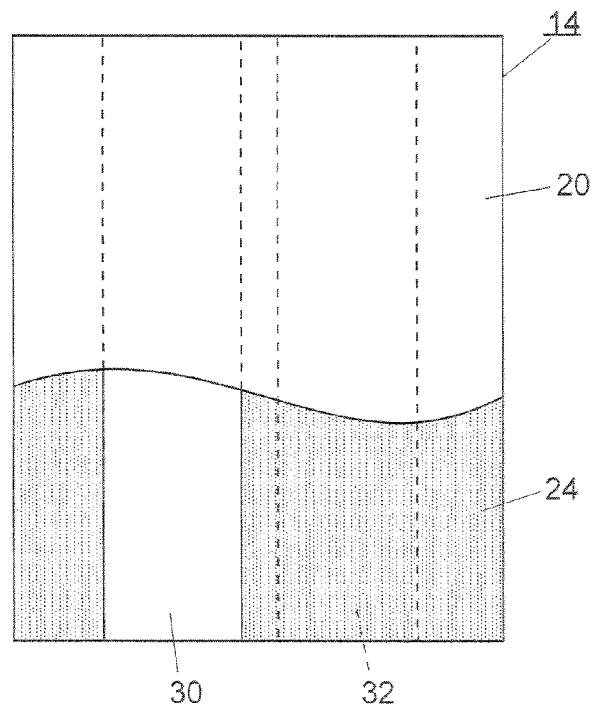
FIG. 2C is a partially cutaway plan view of the suppressor according to the embodiment.

In a case where the ion chromatograph is intended to analyze anions, the suppressor 14 is used to remove cations contained in an eluate through ion exchange. FIGS. 2A to 2C show the suppressor 14 as a first embodiment of a suppressor according to the present invention. The suppressor 14 includes a cover 20 and a base 22 as base bodies. The cover 20 and base 22 are made of an inert material to which ions are not adsorbed and from which ions are not eluted. Examples of such an inert material include acrylic resins and PEEK (polyether ether ketone) resins. Between the cover 20 and the base 22, an ion-exchange membrane 24 is interposed and fixed. The cover 20 has an eluate channel 30 formed therein. The eluate channel 30 has an inlet 26 and an outlet 28 and allows an eluate discharged from the separation column 2 to flow therethrough so that the eluate is brought into contact with the ion-exchange membrane 24. The base 22 has a regenerant channel 32 formed therein. The regenerant channel 32 has an inlet 34 and an outlet 36 and allows a regenerant to flow therethrough so that the regenerant is brought into contact with the ion-exchange membrane 24. The regenerant channel 32 extends in parallel to the eluate channel 30 at such a position that it is not opposed to the eluate channel 30. The eluate channel 30 and the regenerant channel 32 are adjacent to each other, and the distance between the eluate channel 30 and the regenerant channel 32 is set to such a value that ionic functional groups can move from the regenerant channel 32 to the eluate channel 30 through the ion-exchange membrane 24.

The regenerant is pure water or an aqueous solution used to regenerate the ionic functional groups of the ion-exchange membrane 24. The ionic functional groups are hydrogen ions ($H^+$) or hydroxide ions ($OH^-$). More specifically, in a case where the ion-exchange membrane 24 is a cation exchange membrane, the ionic functional groups are hydrogen ions ($H^+$), and in a case where the ion-exchange membrane 24 is an anion exchange membrane, the ionic functional groups are hydroxide ions ($OH^-$).

The eluate channel 30 and the regenerant channel 32 are provided on opposite sides of the ion-exchange membrane 24, but the eluate channel 30 does not have a region opposed to the regenerant channel 32 and the regenerant channel 32 does not have a region opposed to the eluate channel 30. A region opposed to the eluate channel 30, which is on one side of the ion-exchange membrane 24 opposite to the other side of the ion-exchange membrane 24, which is in contact with the eluate channel 30, is supported by the wall surface of the base 22. On the other hand, a region opposed to the regenerant channel 32, which is on the other side of the ion-exchange membrane 24 opposite to the one side of the ion-exchange membrane 24, which is in contact with the regenerant channel 32, is supported by the wall surface of the cover 20. Since a liquid feed pressure is always applied to each of the channels 30 and 32, the ion-exchange membrane 24 is always pressed against the wall surface of the base 22 and the wall surface of the cover 20, thereby preventing the displacement of the ion-exchange membrane 24.

The eluate channel 30 and the regenerant channel 32 are merely hollow channels and are not filled with an obstacle such as a filler.

In a case where the ion chromatograph according to the one embodiment of the present invention is intended to analyze anions, the ion-exchange membrane 24 is a cation exchange membrane. In this case, in the suppressor 14, nontarget cations contained in a col eluate flowing through the eluate channel 30 are selectively removed because they are exchanged for hydrogen ions by adsorption to the ion-exchange membrane 24 and dialysis through the ion-exchange membrane 24. The hydrogen ions exchanged for nontarget cations react with hydroxide ions contained in the column eluate to form water. This reduces the electrical conductivity of the column eluate, thereby reducing noise detected in the electrical conductivity measurement cell 10. The nontarget cations removed by adsorption to the ion-exchange membrane 24 and dialysis through the ion-exchange membrane 24 are exchanged for hydrogen ions contained in a regenerant flowing through the regenerant channel 32 and are discharged into the regenerant.

On the other hand, in a case where the ion chromatograph according to the one embodiment of the present invention is intended to analyze cations, the ion-exchange membrane 24 is an anion exchange membrane. In this case, nontarget anions contained in a column eluate flowing through the eluate channel 30 are selectively removed because they are exchanged for hydroxide ions by the ion-exchange membrane 24. The hydroxide ions exchanged for nontarget anions react with hydrogen ions contained in the column eluate to form water. Therefore, also in this case, the electrical conductivity of the column eluate is reduced, thereby reducing noise detected in the electrical conductivity measurement cell 10. The nontarget anions removed by adsorption to the ion-exchange membrane 24 and dialysis through the ion-exchange membrane 24 are exchanged for hydroxide ions contained in a regenerant flowing through the regenerant channel 32 and are discharged into the regenerant.

Figure 3:
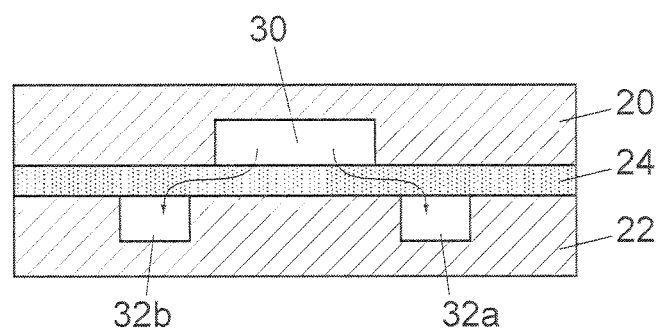
FIG. 3 is a sectional view of a suppressor according to another embodiment of the present invention, taken along a direction perpendicular to the longitudinal direction of channels.

FIG. 3 shows a suppressor according to a second embodiment of the present invention. The suppressor according to the second embodiment is the same as the suppressor according to the first embodiment shown in FIG. 2 in the structure of the eluate channel 30 but is different from that in that it has two regenerant channel 32a and 32b provided on the opposite side of the ion-exchange membrane 24 from the eluate channel 30.

The regenerant channels 32a and 32b are provided on the same surface of the ion-exchange membrane 24 so as not to have a region opposed to the eluate channel 30, and extend in parallel to the eluate channel 30 on opposite sides of the eluate channel 30. A region opposed to the eluate channel 30, which is on one side of the ion-exchange membrane 24 opposite to the other side of the ion-exchange membrane 24, which is in contact with the eluate channel 30, is supported by the wall surface of the base 22. Regions opposed to the regenerant channels 32a and 32b, which are on the other side of the ion-exchange membrane 24 opposite to the one side of the ion-exchange membrane 24, which is in contact with the regenerant channels 32a and 32b, are supported by the wall surface of the cover 20.

A regenerant flows through the regenerant channels 32a and 32b in the same direction, which is opposite to the direction in which an eluate flows through the eluate channel 30.

In the suppressor according to the second embodiment, ionic functional groups of the ion-exchange membrane 24 are supplied from a regenerant flowing through both the regenerant channels 32a and 32b, and nontarget ions contained in an eluate flowing through the eluate channel 30 are removed by exchanging them for ionic functional groups supplied from a regenerant flowing through the regenerant channels 32a and 32b.

Figure 4:
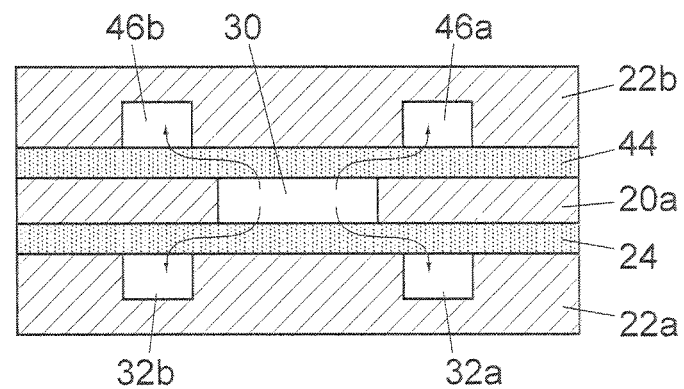
FIG. 4 is a sectional view of a suppressor according to another embodiment of the present invention, taken along a direction perpendicular to the longitudinal direction of channels.

FIG. 4 shows a suppressor according to a third embodiment of the present invention. The suppressor according to the third embodiment has an ion-exchange membrane 44 in addition to the ion-exchange membrane 24 so that these two ion-exchange membranes 24 and 44 are in contact with two different surfaces of the eluate channel 30. The eluate channel 30 is provided as a through-groove in a base body 20a interposed between the two ion-exchange membranes 24 and 44, and has a flat rectangular sectional shape. One of the two opposed sides of the eluate channel 30 is in contact with the ion-exchange membrane 24 and the other side of the eluate channel 30 is in contact with the ion-exchange membrane 44.

On each of the ion-exchange membranes 24 and 44, two regenerant channels are provided in the same manner as those of the suppressor shown in FIG. 3. More specifically, one set of the regenerant channels 32a and 32b is provided in a base body 22a so as to be in contact with one of the two ion-exchange membranes, that is, the ion-exchange membrane 24. The regenerant channels 32a and 32b are provided on the opposite side of the ion-exchange membrane 24 from the eluate channel 30 and extend in parallel to the eluate channel 30 on opposite sides of the eluate channel 30. The other set of regenerant channels 46a and 46b is provided in a base body 22b so as to be in contact with the other ion-exchange membrane 46. The regenerant channels 46a and 46b are provided on the opposite side of the ion-exchange membrane 44 from the eluate channel 30 and extend in parallel to the eluate channel 30 on opposite sides of the eluate channel 30.

A region opposed to the eluate channel 30, which is on one side of the ion-exchange membrane 24 opposite to the other side of the ion-exchange membrane 24, which is in contact with the eluate channel 30, is supported by the wall surface of the base body 22a. Regions opposed to the regenerant channels 32a and 32b, which are on the other side of the ion-exchange membrane 24 opposite to the one side of the ion-exchange membrane 24, which is in contact with the regenerant channels 32a and 32b, are supported by the wall surface of the base body 20a. The other ion-exchange membrane 44 is provided in the same manner as the ion-exchange membrane 24. More specifically, a region opposed to the eluate channel 30, which is on one side of the ion-exchange membrane 44 opposite to the other side of the ion-exchange membrane 44, which is in contact with the eluate channel 30, is supported by the wall surface of the base body 22b. Regions opposed to the regenerant channels 46a and 46b, which are on the other surface of the ion-exchange membrane 44 opposite to the one side of the ion-exchange membrane 44, which is in contact with the regenerant channels 46a and 46b, are supported by the wall surface of the base body 20a.

A regenerant flows through the regenerant channels 32a, 32b, 46a, and 46b in the same direction, which is opposite to the direction in which an eluate flows through the eluate channel 30.

The mechanism of removing nontarget ions from an eluate by the suppressor shown in FIG. 4 is the same as those by the suppressors according to the embodiments shown in FIGS. 2 and 3.

As described above, in the third embodiment shown in FIG. 4, two regenerant channels are in contact with each of the two ion-exchange membranes 24 and 44. However, one regenerant channel may be in contact with one of the two ion-exchange membranes and the other two regenerant channels may be in contact with the other ion-exchange membrane.

Figure 5:
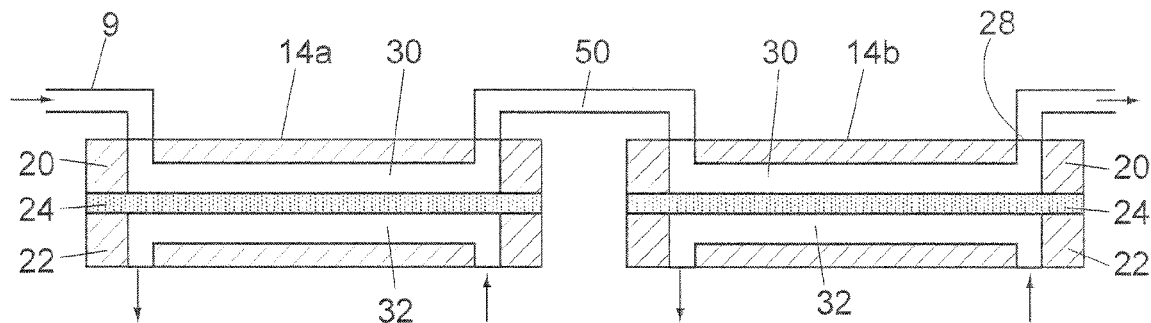
FIG. 5 is a diagram showing the channels according to one embodiment in which two suppressors according to the present invention are connected to each other.

FIG. 5 shows a two-stage suppressor according to another embodiment of the present invention in which the two suppressors according to any one of the above embodiments are connected in series along the flow of a column eluate. More specifically, a suppressor 14a and a suppressor 14b are arranged along an eluate channel 9 on the upstream side and the downstream side, respectively. The eluate outlet of the upstream suppressor 14a is connected to the eluate inlet of the downstream suppressor 14b through a channel 50. An outlet 28 of the downstream suppressor 14b is connected to the electrical conductivity measurement cell 10.

Hereinbelow, the characteristics of the suppressor according to the present invention will be more specifically described with reference to the suppressor shown in FIGS. 2a to 2c. As the ion-exchange membrane 24, an anion exchange membrane having a thickness of 0.01 to 1 mm is used. More specifically, Nafion (registered trademark) is used. The thickness of the Nafion used as the ion-exchange membrane 24 is about 0.2 mm and has sulfonic acid groups to exchange cations contained in an eluate for hydrogen ions. The eluate channel 30 and the regenerant channel 32 each have a width of 1 mm and a depth of 0.1 mm. The length of part of each of the eluate channel 30 and the regenerant channel 32, which is in contact with the ion-exchange membrane 24, is 50 mm. The ion-exchange membrane 24 is interposed between the base 22 and the cover 20 and fixed by interposing these three stacked members between jigs and fixing the jigs by screws.

Figure 6:
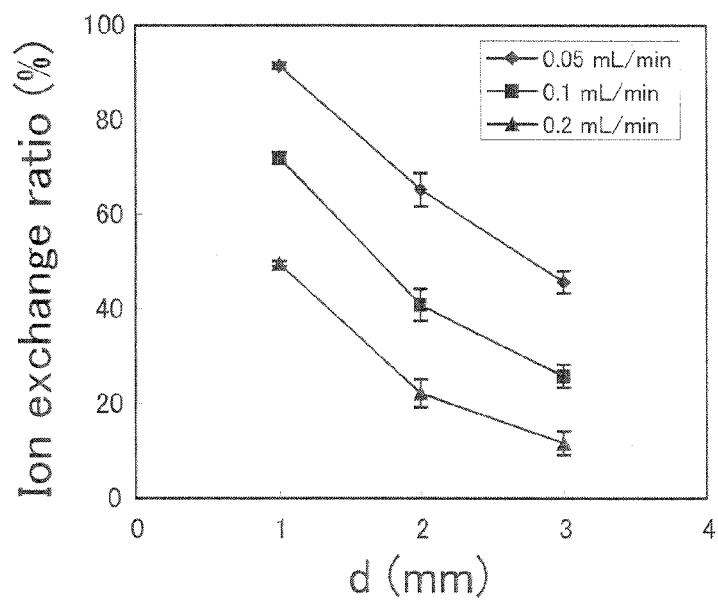
FIG. 6 is a graph showing the performance of the suppressor as one example.
Figure 7A:
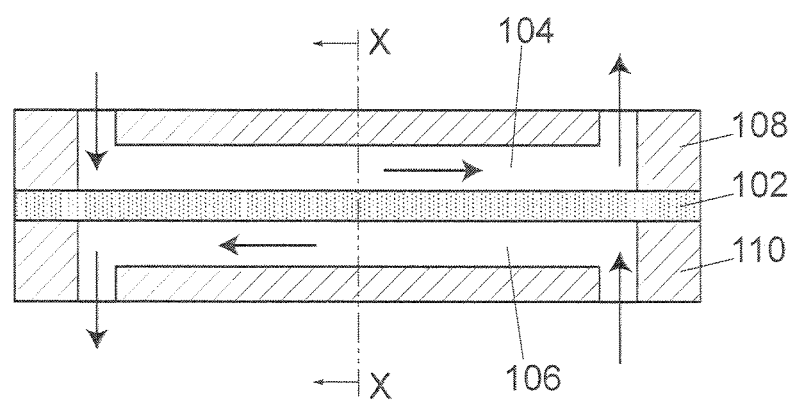
FIG. 7A is a sectional view of a conventional suppressor, taken along the longitudinal direction of channels.
Figure 7B:
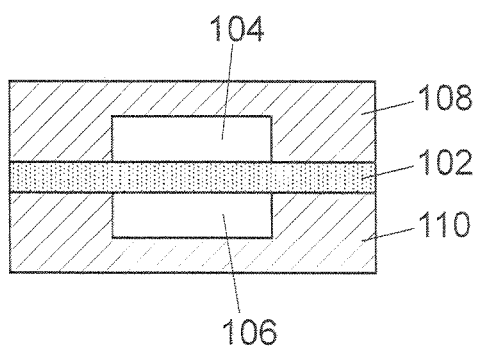
FIG. 7B is a sectional view of the conventional suppressor shown in FIG. 7A, taken along the X-X line.

An ion exchange ratio was measured by changing the distance d between the longitudinal center axis of the eluate channel 30 and the longitudinal center axis of the regenerant channel 32 among three values. The measurement results are shown in FIG. 6. It is to be noted that when the distance d is 1 mm, the distance s between the inner sidewall of the eluate channel 30 and the inner sidewall of the regenerant channel 32 is 0, when the distance d is 2 mm, the distance s is 1 mm, and when the distance d is 3 mm, the distance s is 2 mm.

An alkaline aqueous solution containing 1.8 mmol/L of $Na_2CO_3$ and 1.7 mmol/L of $NaHCO_3$ was used in place of a column eluate allowed to flow through the eluate channel 30. As a regenerant allowed to flow through the regenerant channel 32, 25 mmol/L $H_2SO_4$ was used. The ion exchange ratio was measured under conditions where the flow rate of the regenerant was fixed to 0.2 mL/min and the flow rate of the solution allowed to flow through the eluate channel 30 was changed among three values, 0.05 mL/min, 0.1 mL/min, and 0.2 mL/min. The ion exchange ratio was expressed as the percentage of an ion concentration removed by the suppressor to the ion concentration of the aqueous solution allowed to flow through the eluate channel 30. Since a current value detected by the electrical conductivity measurement cell 10 is proportional to an ion concentration, the ion concentration of the aqueous solution discharged from the suppressor can be determined from a current value detected by the cell 10 based on a previously-prepared calibration curve showing the relationship between the ion concentration of the aqueous solution and a current value detected by the cell 10. An ion concentration removed by the suppressor can be determined by subtracting an ion concentration detected by the electrical conductivity measurement cell 10 from the known ion concentration of the aqueous solution allowed to flow through the eluate channel 30.

As can be seen from the result shown in FIG. 6, a smaller distance between the eluate channel 30 and the regenerant channel 32 increases the ion exchange ratio and a smaller flow rate of the aqueous solution flowing through the eluate channel 30 increases the ion exchange ratio. This is because a smaller flow rate of the aqueous solution flowing through the eluate channel 30 increases the retention time of the aqueous solution in the suppressor, and therefore, the ratio of cations removed through ion exchange is increased in proportion to the retention time.

As described above, the length of each of the channels of this suppressor used is 50 mm, but it is apparent that a higher ion exchange ratio is achieved by a larger channel length. An ideal channel length is about 300 mm.

What is claimed is:

1. A suppressor for suppressing a background electrical conductivity of an eluate discharged from a separation column of an ion analyzer, the suppressor comprising:
   an ion-exchange membrane;
   an eluate channel being in contact with one side of the ion-exchange membrane, the eluate channel serving as a channel through which an eluate discharged from the separation column flows, and having inside no obstacle to the flow;
   a regenerant channel being in contact with the other side of the ion-exchange membrane, the regenerant channel serving as a channel through which a regenerant for regenerating ionic functional groups of the ion-exchange membrane flows, having been disposed so as to have no region opposed to the eluate channel and extending in parallel to the eluate channel in such a nearby position that the ionic functional groups can move to the eluate channel through the ion-exchange membrane, and having inside no obstacle to the flow; and an ion-exchange membrane support member being in contact with at least a region being opposed to the regenerant channel on the one side of the ion-exchange membrane and a region being opposed to the eluate channel on the other side of the ion-exchange membrane, to support the ion-exchange membrane with wall surfaces.

2. The suppressor according to claim 1,
wherein the ion-exchange membrane is interposed between two base bodies so that a laminate structure is formed, and
wherein the eluate channel is provided in one of the base bodies so as to have an inlet and an outlet and to be in contact with the ion-exchange membrane, the regenerant channel is provided in the other base body so as to have an inlet and an outlet and to be in contact with the ion-exchange membrane, and the ion-exchange membrane support member is composed of part of the two base bodies being in contact with the ion-exchange membrane.

3. The suppressor according to claim 1, wherein the regenerant channel is composed of two channels provided on the same surface of the ion-exchange membrane so as to be located on opposite sides of the eluate channel.

4. The suppressor according to claim 1,
wherein the ion-exchange membrane is composed of a first ion-exchange membrane and a second ion-exchange membrane, and
wherein the eluate channel is interposed between the two ion-exchange membranes so that two sides of the eluate channel are in contact with the ion-exchange membranes, and the regenerant channel is provided for each of the ion-exchange membranes.

5. The suppressor according to claim 4,
wherein at least one of the regenerant channels is composed of two channels provided on the same surface of one of the ion-exchange membranes so as to be located on opposite sides of the eluate channel.

6. The suppressor according to claim 4,
wherein the first ion-exchange membrane is in contact with one side of a first base body and is interposed between the first base body and a second base body and the second ion-exchange membrane is in contact with the other side of the first base body and is interposed between the first base body and a third base body so that a laminate structure is formed,
wherein the eluate channel is provided as a groove penetrating the first base body in its thickness direction,
wherein the regenerant channel is composed of a first regenerant channel provided in the second base body so as to have an inlet and an outlet and to be in contact with the first ion-exchange membrane and a second regenerant channel provided in the third base body so as to have an inlet and an outlet and to be in contact with the second ion-exchange membrane, and
wherein the ion-exchange membrane support member is composed of part of the first, second, and third base bodies, which are in contact with the first or second ion-exchange membrane.

7. The suppressor according to claim 1, producing a multistage suppressor provided in a channel through which an eluate discharged from the separation column flows,
wherein the multistage suppressor includes a plurality of the suppressors as upstream and downstream suppressors so that the outlet of the eluate channel of the upstream suppressor is connected to the inlet of the eluate channel of the downstream suppressor.

8. An ion chromatograph comprising:
a separation column;
an eluent supply channel for supplying an eluent to the separation column;
an injector provided in the eluent supply channel for injecting a sample into the eluent supply channel;
an electrical conductivity detector provided in an eluate channel through which an eluate discharged from the separation column flows; and
the suppressor according to claim 1 provided in the eluate channel between the separation column and the electrical conductivity detector.

9. The suppressor according to claim 2, wherein the regenerant channel is composed of two channels provided on the same surface of the ion-exchange membrane so as to be located on opposite sides of the eluate channel.

10. The suppressor according to claim 5,
wherein the first ion-exchange membrane is in contact with one side of a first base body and is interposed between the first base body and a second base body and the second ion-exchange membrane is in contact with the other side of the first base body and is interposed between the first base body and a third base body so that a laminate structure is formed,
wherein the eluate channel is provided as a groove penetrating the first base body in its thickness direction,
wherein the regenerant channel is composed of a first regenerant channel provided in the second base body so as to have an inlet and an outlet and to be in contact with the first ion-exchange membrane and a second regenerant channel provided in the third base body so as to have an inlet and an outlet and to be in contact with the second ion-exchange membrane, and
wherein the ion-exchange membrane support member is composed of part of the first, second, and third base bodies, which are in contact with the first or second ion-exchange membrane.

* * * * *